United States Patent
Miller

(10) Patent No.: US 7,157,421 B2
(45) Date of Patent: Jan. 2, 2007

(54) PIRACETAM AND PIRACETAM ANALOG CONJUGATE AND A PHARMACEUTICAL COMPOSITION FOR TREATMENT OF NEURONAL DISORDERS

(76) Inventor: Landon C. G. Miller, 325 Queens City Ave., Tuscaloosa, AL (US) 35401

( * ) Notice: Subject to any disclaimer, the term of this patent is extended or adjusted under 35 U.S.C. 154(b) by 0 days.

(21) Appl. No.: 11/023,309

(22) Filed: Dec. 27, 2004

(65) Prior Publication Data

US 2006/0142182 A1 Jun. 29, 2006

(51) Int. Cl.
*A01N 37/18* (2006.01)
*A01N 43/00* (2006.01)
*A01N 43/64* (2006.01)
*A01N 43/02* (2006.01)
*A01N 43/16* (2006.01)

(52) U.S. Cl. .................... 514/2; 514/183; 514/185; 514/359; 514/449; 514/451; 514/453; 548/400; 548/416

(58) Field of Classification Search ............. None
See application file for complete search history.

(56) References Cited

U.S. PATENT DOCUMENTS

| | | | |
|---|---|---|---|
| 4,145,347 A | 3/1979 | L'Italien et al. | 546/208 |
| 4,355,027 A | 10/1982 | Growdon et al. | 424/199 |
| 2003/0216466 A1 | 11/2003 | Scheuerman et al. | 514/513 |
| 2004/0092575 A1 | 5/2004 | Peuvot et al. | 514/424 |

OTHER PUBLICATIONS

Piccola, Bolettino Chimico Farmaceutico, 1979, 118(5), 282-285 (English Translation enclosed).*
Piracetam [7491-74-9] from ChemFinder.Com.
Pyrrolidonecarboxylic Acid [98-79-3] from ChemFinder.Com.
Oxiracetam [62613-82-5] from ChemFinder.Com.
Pramiracetam [68497-62-1] from ChemFinder.Com.
Etiracetam [33996-58-6] from ChemFinder.Com.
Aniracetam [72432-10-1] from ChemFinder.Com.
Rolziracetam [18356-28-0] from ChemFinder.Com.

* cited by examiner

*Primary Examiner*—Anish Gupta
*Assistant Examiner*—Satyanarayana R. Gudibande
(74) *Attorney, Agent, or Firm*—Gifford, Krass, Groh, Sprinkle, Anderson & Citkowski, P.C.

(57) ABSTRACT

A compound of the formula

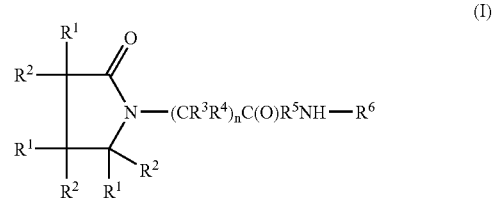

(I)

where $R^1$ is H, $C_1$–$C_4$ alkyl and OH; $R^2$ in is H, $C_1$–$C_4$ alkyl and OH; $R^3$ is H and $C_1$–$C_4$ alkyl; $R^4$ is H and $C_1$–$C_4$ alkyl; n is an integer between 0 and 2 inclusive; $R^5$ is a nullity, $NHR^7C(O)$—, $C_6H_4$—, $C_6H_4$—O—; $R^7$ is $C_2$–$C_6$ alkyl; and $R^6$ is a moiety capable of crossing the blood brain barrier and is as a free compound serotonin, dopamine, blood brain barrier (BBB) peptide, membrane translocating peptide, TAT peptides, bradykinin, beta-endorphin, bombesin, calcitonin, cholecystokinin, an enkephalin, dynorphin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropnin-releasing hormone, growth hormone-releasing hormone, luteinizing hormone, vasoactive intestinal peptidegluconate, transferrin, glucosylamine, amino saccharin, saccharin ester, lactylamine, leucine, tryptophan, amino glutamate and amino cholines.

2 Claims, No Drawings

PIRACETAM AND PIRACETAM ANALOG CONJUGATE AND A PHARMACEUTICAL COMPOSITION FOR TREATMENT OF NEURONAL DISORDERS

FIELD OF THE INVENTION

The subject invention relates to a piracetam or piracetam analog conjugate and synthesis thereof and, more specifically, to the treatment of neuronal disorders by administering the piracetam or piracetam analog conjugate.

BACKGROUND OF THE INVENTION

Piracetam and related pyrrolidine compounds have been shown to improve memory and cognitive learning ability in healthy subjects. Additionally, these compounds appear effective in individuals who have suffered memory or cognitive impairment associated with neuronal conditions or disorders often caused by traumatic brain injury. GABA agonist side effects such as memory loss are also limited by piracetam and/or related pyrrolidine adjunct therapies. This class of compounds has met with limited acceptance in the United States owing to difficulties in administering a form suited to cross the blood brain barrier as well as concerns about piracetam and related pyrrolidine compounds depleting synaptic acetylcholine.

Thus, there exists a need for an improved composition for systemic and/or intrathecal delivery of piracetam and its analogs.

SUMMARY OF THE INVENTION

A compound is provided that has the formula

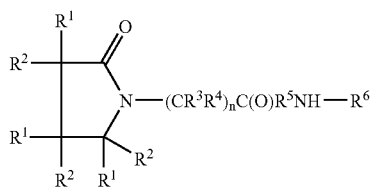

where $R^1$ in each occurrence is independently H, $C_1$–$C_4$ alkyl and OH; $R^2$ in each occurrence is H, $C_1$–$C_4$ alkyl and OH; $R^3$ in each occurrence is H and $C_1$–$C_4$ alkyl; $R^4$ in each occurrence is H and $C_1$–$C_4$ alkyl; n is an integer between 0 and 2 inclusive; $R^5$ is a nullity, $NHR^7C(O)$—, $C_6H_4$—, $C_6H_4$—O—; $R^7$ is $C_2$–$C_6$ alkyl; and $R^6$ is a moiety capable of crossing the blood brain barrier and is as a free compound serotonin, dopamine, blood brain barrier (BBB) peptide, membrane translocating peptide, TAT peptides, bradykinin, beta-endorphin, bombesin, calcitonin, cholecystokinin, an enkephalin, dynorphin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropnin-releasing hormone, growth hormone-releasing hormone, luteinizing hormone, vasoactive intestinal peptidetransferrin, glucosylamine, amino saccharin, lactylamine, leucine, tryptophan, amino glutamate and amino cholines. The compound traverses the blood brain barrier with greater efficiency than piracetam and piracetam analogs thereby reducing side effects associated with systemic piracetam and piracetam analog therapy. A process for forming a conjugate having the formula (I) illustratively includes reacting a piracetam or piracetam analog acid chloride or ester with an amine of a transporter molecule able to traverse the blood brain barrier. The transporter molecule includes serotonin, dopamine, blood brain barrier (BBB) peptide, TAT peptide, glucosylamine, amino saccharin, saccharin ester, lactylamine, leucine, tryptophan, amino glutamate and amino cholines, bradykinin, beta-endorphin, bombesin, calcitonin, cholecystokinin, an enkephalin, dynorphin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropnin-releasing hormone, growth hormone-releasing hormone, luteinizing hormone, vasoactive intestinal peptide transferrin, so as to form an amide bond. The amine of the transporter molecule reacts with the piracetam or piracetam analog to form an amide bond.

DETAILED DESCRIPTION OF THE INVENTION

The present invention provides a method for treating neuronal conditions or disorders often associated with traumatic brain injury, including dystonia/spasticity, spastic disorders, convulsive disorders, tardive dyskinesia, pain or epilepsy by administration to a patient or subject having dystonia/spasticity, a spastic disorder, a convulsive disorder, pain or epilepsy a therapeutically effective amount of a piracetam or piracetam analog conjugate that is able to cross the blood-nerve barrier. Adjunct therapies for facilitating such transport are also provided.

The term "piracetam analog" includes those molecules that contain a pyrrolidone ring having at least one carbonyl containing substituent extending from the nitrogen or a carbon atom of the ring that has a molecular weight of less than 750 and a therapeutic effect in a subject and specifically includes 5-pyrrolidone-2-carboxylic acid, oxiracetam and etiracetam.

The terms "patient" and "subject" are synonymous and mean all animals including humans. Examples of patients or subjects include humans, cows, dogs, cats, goats, sheep, and pigs.

The term "substituted" means that the base organic radical has one or more substituents.

The term "solubility products" means those compounds or compositions formed when a compound is disposed in a solvent.

Those skilled in the art are easily able to identify patients or subjects having dystonia/spasticity, spastic disorders, convulsive disorders, and epilepsy. For example, patients who have sustained traumatic brain injury induced dystonia/spasticity.

A therapeutically effective amount is defined as an amount of a piracetam or piracetam analog conjugate that when administered to a patient or subject, ameliorates a symptom of the condition or disorder.

The compounds of the present invention can be administered to a patient either alone or as part of a pharmaceutical composition. The inventive compositions are suitable for administration to patients by a variety of routes including intrathecally, intraventricularly, intravenously, orally, parenterally, and mucosally.

Compositions suitable for delivery illustratively include physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers; diluents; solvents; or vehicles include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants.

A compound is provided that has the

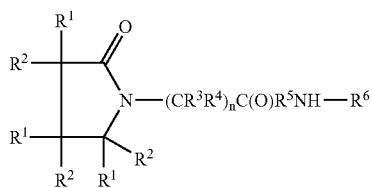

(I)

where $R^1$ in each occurrence is independently H, $C_1$–$C_4$ alkyl and OH; $R^2$ in each occurrence is H, $C_1$–$C_4$ alkyl and OH; $R^3$ in each occurrence is H and $C_1$–$C_4$ alkyl; $R^4$ in each occurrence is H and $C_1$–$C_4$ alkyl; n is an integer between 0 and 2 inclusive; $R^5$ is a nullity, $NHR^7C(O)$—, $C_6H_4$—, $C_6H_4$—O—; $R^7$ is $C_2$–$C_6$ alkyl; and where $R^6$ is a moiety capable of crossing the blood brain barrier and includes as a separate transporter molecule serotonin, dopamine, blood brain barrier (BBB) peptide, membrane translocating peptide, TAT peptide, glucosylamine, amino saccharin, saccharin ester, lactylamine, leucine, tryptophan, amino glutamate and amino cholines, amine containing forms of the following: bradykinin, aminated beta-endorphin, bombesin, calcitonin, cholecystokinin, an enkephalin, dynorphin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropnin-releasing hormone, growth hormone-releasing hormone, luteinizing hormone, vasoactive intestinal peptide transferrin, aminated glucose, aminated L-lactate, L-leucine, L-glutamate, aminated saccharin and aminated choline. An inventive compound being formed preferably through the reaction of a pyrrolidine ester with a primary or secondary amine transporter, the ester having the formula:

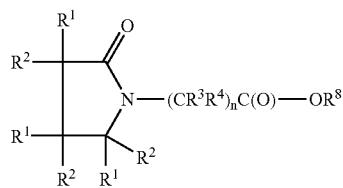

where $R^1$–$R^4$ are as previously described and $R^8$ is a $C_1$–$C_{12}$ alkyl. Alternatively, a pyrrolidine acid chloride of the formula:

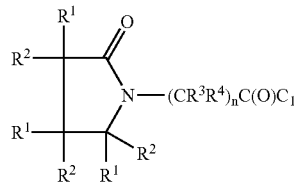

where $R^1$–$R^5$ are as previously described is reacted with a transporter amine.

According to the present invention, a piracetam or piracetam analog conjugate compound is formed to a species known to traverse the blood brain barrier either through diffusion or a specific transporter. While the specific transport mechanism is unclear, owing to the small molecular weight and lack of steric hindrance associated with gamma-aminobutyramide, inhibitory affects on the transporter species associated with conjugation are limited.

In a preferred embodiment, an inventive conjugate compound includes a transporter moiety $R^6$ having a privileged ability to pass the blood brain barrier and thereafter be cleaved from a piracetam or piracetam analog component to itself form an active therapeutic or neurochemistry equilibrium modifier. The ability to deliver as a conjugate a piracetam or piracetam analog with a second neuroactive species provides a previously unavailable ability to moderate a neurological therapeutic effect. As neuroactive compounds are subject to complex feedback mechanisms, the successful transport of a compound across the blood brain barrier has a moderated therapeutic effect owing to neurochemistry equilibrium shifts in response to the compound traversing the barrier. An inventive conjugate provides piracetam or piracetam analog that upon cleavage from the transporter moiety $R^6$ is in proximity to a second neurologically active species that has an agonistic, antagonistic, or independently operating neuroactive species. The piracetam or piracetam analog and moiety $R^6$ after cleavage being subject to further enzymatic modification and/or efflux clearance. It is appreciated that two or more inventive conjugates are amenable to simultaneous delivery in order to provide still more refined therapeutic affects.

An inventive conjugate compound is preferably formed through an amide linkage between a piracetam or piracetam analog ester or carboxylic acid and a primary or secondary aminated blood brain barrier transporter compound. Aminated blood brain barrier transporter compounds operative herein illustratively include serotonin, blood brain barrier (BBB) peptide, membrane translocating peptide, dopamine, transferrin, TAT peptides, bradykinin, beta-endorphin, bombesin, calcitonin, cholecystokinin, an enkephalin, dynorphin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropnin-releasing hormone, growth hormone-releasing hormone, luteinizing hormone, vasoactive intestinal peptidegluconate, aminated glucose, aminated L-lactate, L-leucine, L-glutamate, aminated saccharin and aminated choline. The aminated or phosphorylated transporter compound is reacted with a piracetam or piracetam analog ester or carboxylic acid, the pyrrolidine amide having a nitrogen substituent that is able to cross the blood brain barrier transporter. Alternatively a pyrrolidine acid chloride is conjugated to a blood brain barrier transporter compound. Preferably a pyrrolidine amine is reacted with a blood brain transporter compound ester.

Carbodiimides are zero length cross-linkers that mediate the formation of an amide or phosphoramidate linkage between a carboxylate and an amine, or a phosphate and an amine, respectively. Chu, B., Kramer, F. & Orgel, L. (1986), "Synthesis of an amplifiable reporter RNA for bioassays," Nucleic Acids Research, 14, 5591–5603. Hoare, D. & Koshland, D. E. (1966) J. Am. Chem. Soc., 88, 2057. Carbodiimides react with carboxylic acids to form highly reactive O-acylisourea compounds that are very short lived but react with nucleophiles to form an amide bond. Dicyclohexylcarbodiimide (DCCD) is representative of a reactive carbodiimide. This reaction works effectively between pH 4.5 and 7.5. Molecules with a phosphate group such as the 5' phosphate on oligonucleotides can also react with amine-containing groups by using the carbodiimide reaction.

Optionally, a linker species is provided intermediate between the transporter moiety $R^6$ and the aminobutyramide portion of an inventive conjugate. The linker in simplest form includes a moiety reactive with the pendant carbonyl carbon of the piracetam or piracetam analog precursor and a second moiety reactive with the transporter compound. Substituents extending from a linker are provided to modify the lipophilicity of an inventive conjugate, or tether a dye or spectroscopic marker. With the inclusion of a linker, care should be taken to limit both the molecular weight and the hydrophilicity of the linker in order to retain the ability to traverse the blood brain barrier. Typically, the linker has eight or less backbone carbon atoms. Preferably, the linker backbone is linked to the piracetam or piracetam analog amido portion of an inventive conjugate compound through an oxygen atom or a carbon atom. The linker moiety reactive with the piracetam or piracetam analog portion carbonyl carbon illustratively form an amide and an ester linkage. Transporter compound reactive moiety of the linker is dependent upon the transporter compound moiety to be bound thereto. Suitable chemistries for a variety of potential reaction moieties are found in *Comprehensive Organic Transformations*, R. C. Larock, John Wiley & Sons 1999.

It is appreciated that a linker, when present, is the preferred site for the attachment of an additional species. A substituent is optionally provided pendent from the linker backbone. The substituent illustratively includes a radioactive atom, a magnetic spectroscopically active marker and an organic dye. A radioactive atom is alternatively operative as a marker in isotope studies such as positron emission tomography, single photon emission computer tomography, radiological studies and the like. Common radio-isotopes used in medical imaging illustratively include $^{123}$I, $^{99m}$Tc, and other chelated radioisotopes as detailed in U.S. Pat. No. 6,241,963. Spectroscopically active markers include NMR/MRI active contrast enhancing moieties known to the art such as gadolinium, as detailed in Contrast Agents 1: Magnetic Resonance Imaging (Topics in Current Chemistry, 221) by Werner Krause, Springer Verlag, Berlin, Germany. Organic dyes, while recognized to have potentially distinct NMR/MRI signatures, are provided to yield an optically active spectroscopic signature suitable for biopsy, surgical identification, or preclinical studies of tissue treated by an inventive compound.

Optionally, an inventive conjugate is administered in combination with acetylcholine or an acylglycerophosphocholine as provided in U.S. Pat. No. 4,355,027 to counter the propensity of piracetam and piracetam analogs to deplete neural acetylcholine. Acetylcholine depletion is considered especially problematic over a prolonged therapeutic regime.

Compositions suitable for injection optionally include physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

The enteric coating is typically a polymeric material. Preferred enteric coating materials have the characteristics of being bioerodible, gradually hydrolyzable and/or gradually water-soluble polymers. The amount of coating material applied to a solid dosage generally dictates the time interval between ingestion and drug release. A coating is applied with to a thickness such that the entire coating does not dissolve in the gastrointestinal fluids at pH below 5 associated with stomach acids, yet dissolves above pH 5 in the small intestine environment. It is expected that any anionic polymer exhibiting a pH-dependent solubility profile is readily used as an enteric coating in the practice of the present invention to achieve delivery of the active to the lower gastrointestinal tract. The selection of the specific enteric coating material depends on properties such as resistance to disintegration in the stomach; impermeability to gastric fluids and active agent diffusion while in the stomach; ability to dissapate at the target intestine site; physical and chemical stability during storage; non-toxicity; and ease of application.

Suitable enteric coating materials illustratively include cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropyhnethyl cellulose succinate and carboxymethylcellulose sodium; acrylic acid polymers and copolymers, preferably formed from acrylic acid, methacrylic acid, methyl acrylate, ammonio methylacrylate, ethyl acrylate, methyl methacrylate and/or ethyl; vinyl polymers and copolymers such as polyvinyl pyrrolidone, polyvinyl acetate, polyvinylacetate phthalate, vinylacetate crotonic acid copolymer, and ethylene-vinyl acetate copolymers; shellac; and combinations thereof. A particularly preferred enteric coating material for use herein are those acrylic acid polymers and copolymers available under the tradename EUDRAGIT®, Roehm Pharma (Germany). The EUDRAGIT® series L, L-30D and S copolymers are most preferred since these are insoluble in stomach and dissolve in the intestine.

The enteric coating provides for controlled release of the active agent, such that release is accomplished at a predictable location in the lower intestinal tract below the point at which drug release would occur absent the enteric coating. The enteric coating also prevents exposure of the active agent and carrier to the epithelial and mucosal tissue of the buccal cavity, pharynx, esophagus, and stomach, and to the enzymes associated with these tissues. The enteric coating therefore helps to protect the active agent and a patient's internal tissue from any adverse event prior to drug release at the desired site of delivery. Furthermore, the coated solid dosages of the present invention allow optimization of drug absorption, active agent protection, and safety. Multiple enteric coatings targeted to release the active agent at various regions in the lower gastrointestinal tract would enable even more effective and sustained improved delivery throughout the lower gastrointestinal tract.

The enteric coating optionally contains a plasticizer to prevent the formation of pores and cracks that allow the penetration of the gastric fluids into the solid dosage. Suitable plasticizers illustratively include, triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, a coating composed of an anionic carboxylic acrylic polymer typically contains approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g., hydroxypropylcellulose, acids and bases) to solubilize or disperse the coating material, and to improve coating performance and the coated product.

The enteric coating is applied to a solid dosage using conventional coating methods and equipment. For example, an enteric coating can be applied to a solid dosage using a coating pan, an airless spray technique, fluidized bed coating equipment, or the like. Detailed information concerning materials, equipment and processes for preparing coated dosage forms may be found in Pharmaceutical Dosage Forms: Tablets, eds. Lieberman et al. (New York: Marcel Dekker, Inc., 1989), and in Ansel et al., Pharmaceutical Dosage Forms and Drug Delivery Systems, 6.sup.th Ed. (Media, Pa.: Williams & Wilkins, 1995).

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

An inventive compound is also delivered in conjunction with an active therapeutic compound. The therapeutic compound illustratively being active as antibiotic, a gamma or beta radiation emitting species, an anti-inflammatory, an antitumoral, an antiviral, an antibody, a hormone, an enzyme, and antigenic peptide or protein.

The examples presented below are intended to illustrate particular embodiments of the invention and are not intended to limit the scope of the specification, including the claims.

EXAMPLES

Example 1

Preparation of serotoninyl-2-oxo-1-pyrrolidine acetamide

A mixture of ethyl 2-oxo-pyrrolidine acetate (5 mmol) and serotonin (5 mmol) in 200 ml tetrahydrofuran is heated to 70° C. for 24 hours. The resulting serotininyl-2-oxo-1-pyrrolidine acetamide is collected as an oil and purified to pharmaceutical purity.

Example 2

Preparation of Lactyl Piracetam

A mixture of ethyl 2-oxo-pyrrolide acetyl chloride is cooled to −10° C. in $CH_2Cl_2$ (200 ml) and 5 mmol of lactyl amine is added in 10 ml CH$_2$Cl$_2$ followed by triethylamine (15 mmol) under N$_2$. The resulting lactyl piracetam is collected as an oil and purified to pharmaceutical purity.

Example 3

Preparation of Amido Glycosyl Etiracetam

The procedure of Example 2 is repeated with the substitution of a stoichiometric amount of 2 glucosylamine for lactyl amine to produce the title compound.

Example 4

Preparation of Transferrin Piracetamide

The preparation of Example 1 is repeated with the substitution of a stoichiometric amount of transferrin for serotonin and the heating to 60° C. for 40 hours to produce the title compound.

Patent applications and publications mentioned in the specification are indicative of the levels of those skilled in the art to which the invention pertains. These applications and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

What is claimed is:

1. A conjugate compound having the formula

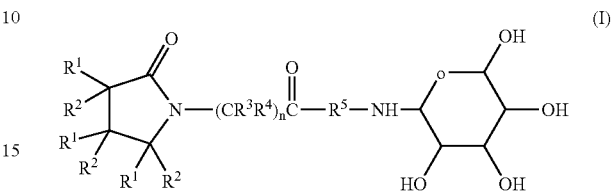

where R$^1$ in each occurrence is independently H, C$_1$–C$_4$ alkyl or OH; R$^2$ in each occurrence is H, C$_1$–C$_4$ alkyl or OH; R$^3$ in each occurrence is H or C$_1$–C$_4$ alkyl; R$^4$ in each occurrence is H or C$_1$–C$_4$ alkyl; n is an integer between 0 and 2 inclusive; R$^5$ is absent, NHR$^7$C(O)—, C$_6$H$_4$—, or C$_6$H$_4$—O—; R$^7$ is C$_2$–C$_6$ alkyl.

2. A composition comprising the compound of claim 1.

* * * * *